US012721861B2

(12) United States Patent
Mitragotri et al.

(10) Patent No.: US 12,721,861 B2
(45) Date of Patent: Sep. 1, 2026

(54) DELIVERY AND RETENTION OF ACTIVE AGENTS WITHIN THE SKIN

(71) Applicant: Fount Bio, Inc., Cambridge, MA (US)

(72) Inventors: Samir Mitragotri, Lexington, MA (US); Eric Spengler, Cambridge, MA (US); Douglas Levinson, Sherborn, MA (US); Douglas R. Vogus, Cambridge, MA (US)

(73) Assignee: Fount Bio, Inc., Cambridge, MA (US)

( * ) Notice: Subject to any disclaimer, the term of this patent is extended or adjusted under 35 U.S.C. 154(b) by 1051 days.

(21) Appl. No.: 17/602,110

(22) PCT Filed: Apr. 17, 2020

(86) PCT No.: PCT/US2020/028639
§ 371 (c)(1),
(2) Date: Oct. 7, 2021

(87) PCT Pub. No.: WO2020/214889
PCT Pub. Date: Oct. 22, 2020

(65) Prior Publication Data

US 2022/0175819 A1 Jun. 9, 2022

Related U.S. Application Data

(60) Provisional application No. 62/836,402, filed on Apr. 19, 2019.

(51) Int. Cl.
*A61K 31/728* (2006.01)
*A61K 8/73* (2006.01)
*A61K 47/54* (2017.01)
*A61Q 19/00* (2006.01)

(52) U.S. Cl.
CPC ............ *A61K 31/728* (2013.01); *A61K 8/735* (2013.01); *A61K 47/545* (2017.08); *A61Q 19/00* (2013.01); *A61K 2800/413* (2013.01)

(58) Field of Classification Search
CPC .... A61Q 19/00; A61K 47/545; A61K 31/728; A61K 8/735; A61K 8/73; A61K 2800/413
See application file for complete search history.

(56) References Cited

U.S. PATENT DOCUMENTS 8,038,991 B1 10/2011 Stankus et al.
9,932,333 B2 4/2018 Kanai et al.
10,624,865 B2 4/2020 Pathak
(Continued)

FOREIGN PATENT DOCUMENTS

CA 3118491 A1 5/2020
CN 109310625 A 2/2019
(Continued)

OTHER PUBLICATIONS

Dubikovskaya, E. et al., Precursor molecules for the synthesis of D-luciferin, WO2014057139A2, pp. 1-2 (2014).
(Continued)

*Primary Examiner* — Hong Yu
(74) *Attorney, Agent, or Firm* — Choate, Hall & Stewart LLP; Brenda Herschbach Jarrell; Lauren E. Markham

(57) ABSTRACT

The present application describes the synthesis, formulation and uses of systems comprising agents capable of penetrating skin.

11 Claims, 4 Drawing Sheets

(56) References Cited

U.S. PATENT DOCUMENTS

| | | | | |
|---|---|---|---|---|
| 11,013,670 | B2 | 5/2021 | Kim et al. | |
| 12,311,048 | B2 | 5/2025 | Mitragotri et al. | |
| 2004/0127699 | A1 | 7/2004 | Zhao et al. | |
| 2006/0008428 | A1 | 1/2006 | Seyler et al. | |
| 2006/0159714 | A1* | 7/2006 | Thorel | A61K 31/375 424/70.13 |
| 2007/0142575 | A1 | 6/2007 | Zheng et al. | |
| 2009/0156480 | A1* | 6/2009 | Akashi | A61K 39/35 977/773 |
| 2009/0263843 | A1* | 10/2009 | Anderson | C07D 417/14 530/344 |
| 2011/0223625 | A1* | 9/2011 | Kelts | C07K 5/1005 435/8 |
| 2013/0096081 | A1 | 4/2013 | Njikang et al. | |
| 2013/0108550 | A1* | 5/2013 | Trollsas | A61K 49/0054 424/9.1 |
| 2013/0165463 | A1 | 6/2013 | Gurtner et al. | |
| 2013/0287699 | A1* | 10/2013 | Chang | G01N 33/582 424/9.6 |
| 2014/0227174 | A1 | 8/2014 | Muraski et al. | |
| 2014/0256831 | A1 | 9/2014 | Ito et al. | |
| 2017/0348218 | A1 | 12/2017 | Chen et al. | |
| 2018/0186900 | A1 | 7/2018 | Mitragotri et al. | |
| 2023/0165780 | A1 | 6/2023 | Mitragotri et al. | |
| 2025/0312265 | A1 | 10/2025 | Mitragotri et al. | |
| 2025/0339365 | A1 | 11/2025 | Levinson et al. | |

FOREIGN PATENT DOCUMENTS

| | | | |
|---|---|---|---|
| JP | 2009-519239 | A | 5/2009 |
| JP | 2016-106112 | A | 6/2016 |
| WO | WO-2007/064773 | A2 | 6/2007 |
| WO | WO-2008/016983 | A2 | 2/2008 |
| WO | WO-2009/108100 | A1 | 9/2009 |
| WO | WO-2012/010704 | A1 | 1/2012 |
| WO | WO-2013/159064 | A1 | 10/2013 |
| WO | WO-2014/057139 | A2 | 4/2014 |
| WO | WO-2014/178878 | A1 | 11/2014 |
| WO | WO-2016/010092 | A1 | 1/2016 |
| WO | WO-2016/201382 | A1 | 12/2016 |
| WO | WO-2017/173026 | A1 | 10/2017 |
| WO | WO-2020/093022 | A1 | 5/2020 |
| WO | WO-2020/214889 | A1 | 10/2020 |

OTHER PUBLICATIONS

International Search Report for PCT/US20/28639 (Delivery and Retention of Active Agents Within the Skin, filed Apr. 17, 2020), received by ISA/EP, 7 pages (Jul. 1, 2020).

International Search Report for PCT/US2019/059553 (Crosslinked Materials, filed Nov. 1, 2019), received from ISA/EP, 5 pages (Feb. 21, 2020).

International Search Report for PCT/US2021/056916, 5 pages (Feb. 8, 2022).

Ng, K.W. and Lau, W.M., Skin Deep: The Basics of Human Skin Structure and Drug Penetration, N. Dragicevic, H.I. Maibach (eds.), *Percutaneous Penetration Enhancers Chemical Methods in Penetration Enhancement: Drug Manipulation Strategies and Vehichle Effects*, Springer-Verlag Berlin Heidelberg, 9 pages (2015).

Ruan, S. et al., Ligand-Mediated and Enzyme-Directed Precise Targeting and Retention for the Enhanced Treatement of Glioblastoma, ACS Appl. Mater. Interfaces., 9:20348-20360 (2017).

Wang, P. et al., Site-specific immobilization of biomolecules by a biocompatable reaction between terminal cysteine and 2-cyanobenzothiazole, Chem. Commun., 49:8644-8646 (2013).

Wang, Z. et al., Hierarchical Assembly of Bioactive Amphiphilic Molecule Pairs into Supramolecular Nanofibril Self-Supportive Scaffolds for Stem Cell Differentiation, J. Am. Chem. Soc., 138:15027-15034 (2016).

Written Opinion for PCT/US20/28639 (Delivery and Retention of Active Agents Within the Skin, filed Apr. 17, 2020), received by ISA/EP, 10 pages (Jul. 1, 2020).

Written Opinion for PCT/US2019/059553 (Crosslinked Materials, filed Nov. 1, 2019), received from ISA/EP, 9 pages (Feb. 21, 2020).

Written Opinion for PCT/US2021/056916, 9 pages (Feb. 8, 2022).

Yuan, Y. et al., Intracellular Self-Assembly of Taxol Nanoparticles for Overcoming Multidrug Resistance, Angew. Chem. Int. Ed., 54:9700-9704 (2015).

Zhang, X. et al., Improved method for synthesis of cysteine modified hyaluronic acid for in situ hydrogel formation, Chemical Communications, 51:9662-9665 (2015).

Ruan, S., Ligand-Mediated and Enzyme-Directed Precise Targeting and Retention for the Enhanced Treatment of Glioblastoma, ACS Applied Materials& Inferfaces vol. 9, No. 24 (2017).

Wang, Z. et al., Supplementary Material for Hierarchical Assembly of Bioactive Amphiphilic Molecule Pairs into Supramolecular Nanofibril Self-Supportive Scaffolds for Stem Cell Differentiation, XP055706252 (2016).

Casale, J. and Crane, U.S., Biochemistry, Glycosaminoglycans. [Updated Mar. 27, 2023]. In: StatPearls [Internet]. Treasure Island (FL): StatPearls Publishing; Jan. 2024-. Available from: https://www.ncbi.nlm.nih.gov/books/NBK544295/.

Iris Biotech, Cyanobenzothiazole (CBT) Derivatives for "Click" Conjugation, retrieved from: https://iris-biotech.de/en/blog/cyanobenzothiazole-cbt-derivatives-for-click-conjugation.html, 10 pages (Jul. 25, 2023).

Menegatti, S. et al., Synthesis and characterization of a self-fluorescent hyaluronic acid-based gel for dermal applications, Adv Health Mater., 4(15):2297-305 (2015).

* cited by examiner

HA-CBT gly-CBT

DELIVERY AND RETENTION OF ACTIVE AGENTS WITHIN THE SKIN

RELATED APPLICATIONS

This application claims the benefit under 35 U.S.C. § 371 of International Application No. PCT/US20/28639, filed Apr. 17, 2021, which claims the benefit of and priority to U.S. Provisional Patent Application No. 62/836,402, filed Apr. 19, 2019, the entire contents of each of which is hereby incorporated by reference.

SUMMARY

The present disclosure provides a variety of insights relating to carriers for delivering and retaining molecules that confer therapeutic or cosmetic activity in the skin. The ability to deliver and/or retain cosmetic or therapeutic agents within the skin is highly desirable. In many cases, enhancing the delivery and/or retention of such agents can significantly increase the efficacy and safety of treatment. Among other things, the present disclosure provides for use of 6-amino-2-cyanobenzothiazole (CBT), and its analogs, to enhance the delivery and/or retention of such actives.

DEFINITIONS

Figure 1:
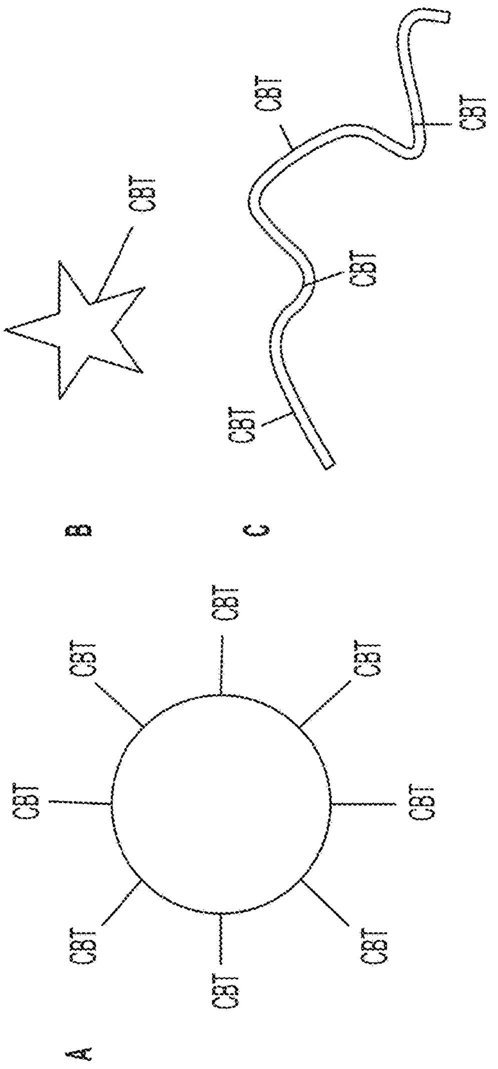
FIG. 1, comprising panels A-C, illustrates CBT functionalized entities: example of particle decorated with CBT (A), active functionalized with a single CBT moiety (B), and active functionalized with multiple CBT moieties (C).

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Aliphatic: The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "carbocyclic", "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 carbon atoms. In some embodiments, aliphatic groups contain 1-4 carbon atoms. In some embodiments, aliphatic groups contain 1-3 carbon atoms, and in some embodiments, aliphatic groups contain 1-2 carbon atoms. In some embodiments, "carbocyclic" (or "cycloaliphatic" or "carbocycle" or "cycloalkyl") refers to a monocyclic $C_3$-$C_8$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

Alkylene: The term "alkylene" refers to a bivalent alkyl group. An "alkylene chain" is a polymethylene group, i.e., $—(CH_2)_n—$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

Aryl: The term "aryl" used alone or as part of a larger moiety as in "aralkyl," "aralkoxy," or "aryloxyalkyl," refers to ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system and exemplary groups include phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

Associated: Two events or entities are "associated" with one another, as that term is used herein, if the presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biocompatible: The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Corresponding to: As used herein in the context of polypeptides, nucleic acids, and chemical compounds, the term "corresponding to", designates the position/identity of a structural element, e.g., of an amino acid residue, a nucleotide residue, or a chemical moiety, in a compound or composition through comparison with an appropriate reference compound or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polymer may be designated using a canonical numbering system based on a reference related polymer, so that a residue "corresponding to" one at position 190 of a reference polymer, for example, need not actually be the $190^{th}$ residue in a polymer of interest, but rather refers to the residue that corresponds to the residue found at position 190 in the reference polymer; those of ordinary skill in the art readily appreciate how to identify "corresponding" residues in polymers (e.g., using commercially available sequence comparison software for polypeptide and nucleic acid polymers; optionally manually for other polymers).

Designed: As used herein, the term "designed" refers to an agent (i) whose structure is or was selected by the hand of man; (ii) that is produced by a process requiring the hand of man; and/or (iii) that is distinct from natural substances and other known agents.

Dosage form: Those skilled in the art will appreciate that the term "dosage form" may be used to refer to a physically discrete unit of an agent (e.g., a therapeutic, diagnostic or cosmetic agent) for administration to a subject. Typically, each such unit contains a predetermined quantity of agent. In some embodiments, such quantity is a unit dosage amount (or a whole fraction thereof) appropriate for administration in accordance with a dosing regimen that has been determined to correlate with a desired or beneficial (e.g., therapeutic and/or cosmetic) outcome when administered to a relevant population (i.e., with a therapeutic dosing regimen). In some embodiments, such quantity is a unit dosage amount (or a whole fraction thereof) appropriate for administration in accordance with a regimen that has been determined to correlate with a desired or beneficial cosmetic outcome (e.g., provides visible and/or tactile improvement to skin) when administered to a relevant population. Those of ordinary skill in the art appreciate that the total amount of a composition or agent administered to a particular subject is determined by one or more attending professionals (e.g., physicians, nurses, or other licensed professionals) and may involve administration of multiple dosage forms. In some embodiments, a dosage form may be provided in a formulation that is or comprises a cream, gel, liquid, lotion, mist, mask, matrix, particle, paste, patch, powder, serum, solid, spray (or collection thereof), or a combination thereof.

Dosing regimen: Those skilled in the art will appreciate that the term "dosing regimen" may be used to refer to a set of unit doses (typically more than one) that are administered individually to a subject, typically separated by periods of time. In some embodiments, a given agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population.

Excipient: As used herein, the term "excipient" refers to an inactive (e.g., not a therapeutic active such as a cosmetic active) agent that may be included in a pharmaceutical composition, for example to provide or contribute to a desired consistency or stabilizing effect.

Halogen: The term "halogen" means F, Cl, Br, or I.

Heteroaryl: The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and/or having, in addition to carbon atoms, from one to five heteroatoms wherein the term "heteroatom" refers to nitrogen, oxygen, or sulfur, and includes any oxidized form of nitrogen or sulfur, and any quaternized form of a basic nitrogen. Exemplary heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Exemplary groups include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

Heterocycle: As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}NR$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

"Improve," "increase", "inhibit" or "reduce": As used herein, the terms "improve", "increase", "inhibit", "reduce", or grammatical equivalents thereof, indicate values that are relative to a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment.

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients.

Linker: as used herein, is used to refer to that portion of a multi-element agent that connects different elements to one another.

Marker: A marker, as used herein, refers to an entity or moiety whose presence or level is a characteristic of a particular state or event. In some embodiments, presence or level of a particular marker may be characteristic of presence, state, or stage of a disease, disorder, or condition.

Optionally Substituted: As described herein, compounds may sometimes contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g.,

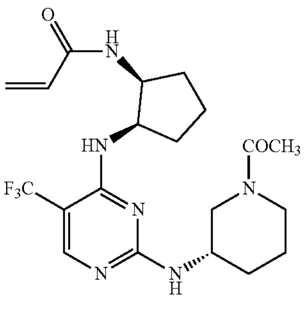 [SMILES: C=CC(=O)N[C@H]1CCC[C@H]1Nc1nc(N[C@H]2CCCN(C(C)=O)C2)ncc1C(F)(F)F]

refers to at least

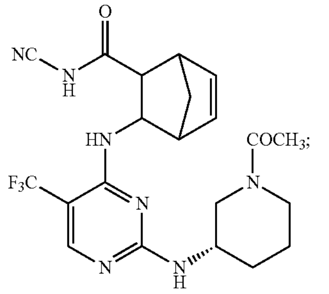

and

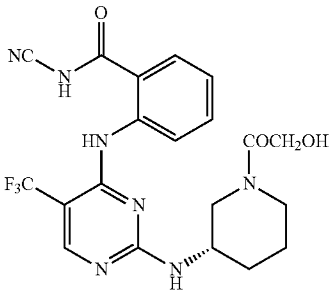

refers to at least

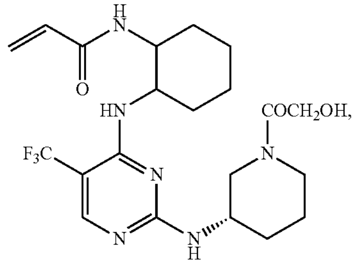

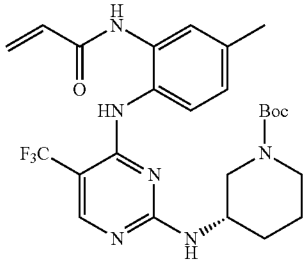

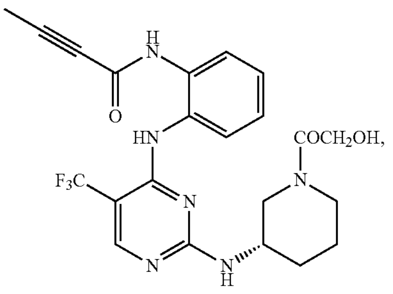

or

-continued

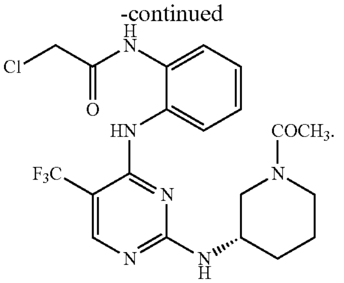

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. Suitable monovalent substituents on a substitutable carbon atom of an "optionally substituted" group are independently halogen; $—(CH_2)_{0-4}R^{\circ}$; $—(CH_2)_{0-4}OR^{\circ}$; $—O(CH_2)_{0-4}R^{\circ}$, $—O—(CH_2)_{0-4}C(O)OR^{\circ}$; $—(CH_2)_{0-4}CH(OR^{\circ})_2$; $—(CH_2)_{0-4}SR^{\circ}$; $—(CH_2)_{0-4}Ph$, which may be substituted with $R^{\circ}$; $—(CH_2)_{0-4}O(CH_2)_{0-1}Ph$ which may be substituted with $R^{\circ}$; $—CH{=}CHPh$, which may be substituted with $R^{\circ}$; $—(CH_2)_{0-4}O(CH_2)_{0-1}$-pyridyl which may be substituted with $R^{\circ}$; $—NO_2$; $—CN$; $—N_3$; $—(CH_2)_{0-4}N(R^{\circ})_2$; $—(CH_2)_{0-4}N(R^{\circ})C(O)R^{\circ}$; $—N(R^{\circ})C(S)R^{\circ}$; $—(CH_2)_{0-4}N(R^{\circ})C(O)NR^{\circ}_2$; $—N(R^{\circ})C(S)NR^{\circ}_2$; $—(CH_2)_{0-4}N(R^{\circ})C(O)OR^{\circ}$; $—N(R^{\circ})N(R^{\circ})C(O)R^{\circ}$; $—N(R^{\circ})N(R^{\circ})C(O)NR^{\circ}_2$; $—N(R^{\circ})N(R^{\circ})C(O)OR^{\circ}$; $—(CH_2)_{0-4}C(O)R^{\circ}$; $—C(S)R^{\circ}$; $—(CH_2)_{0-4}C(O)OR^{\circ}$; $—(CH_2)_{0-4}C(O)SR^{\circ}$; $—(CH_2)_{0-4}C(O)OSiR^{\circ}_3$; $—(CH_2)_{0-4}OC(O)R^{\circ}$; $—OC(O)(CH_2)_{0-4}SR—$, $SC(S)SR^{\circ}$; $—(CH_2)_{0-4}SC(O)R^{\circ}$; $—(CH_2)_{0-4}C(O)NR^{\circ}_2$; $—C(S)NR^{\circ}_2$; $—C(S)SR^{\circ}$; $—SC(S)SR^{\circ}$, $—(CH_2)_{0-4}OC(O)NR^{\circ}_2$; $—C(O)N(OR^{\circ})R^{\circ}$; $—C(O)C(O)R^{\circ}$; $—C(O)CH_2C(O)R^{\circ}$; $—C(NOR^{\circ})R^{\circ}$; $—(CH_2)_{0-4}SSR^{\circ}$; $—(CH_2)_{0-4}S(O)_2R^{\circ}$; $—(CH_2)_{0-4}S(O)_2OR^{\circ}$; $—(CH_2)_{0-4}OS(O)_2R^{\circ}$; $—S(O)_2NR^{\circ}_2$; $—(CH_2)_{0-4}S(O)R^{\circ}$; $—N(R^{\circ})S(O)_2NR^{\circ}_2$; $—N(R^{\circ})S(O)_2R^{\circ}$; $—N(OR^{\circ})R^{\circ}$; $—C(NH)NR^{\circ}_2$; $—P(O)_2R^{\circ}$; $—P(O)R^{\circ}_2$; $—OP(P)R^{\circ}_2$; $—OP(O)(OR^{\circ})_2$; $SiR^{\circ}_3$; $—(C_{1-4}$ straight or branched)alkylene)O—$N(R^{\circ})_2$; or $—(C_{1-4}$ straight or branched)alkylene)C(O)O—$N(R^{\circ})_2$, wherein each $R^{\circ}$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below. Suitable monovalent substituents on $R^{\circ}$ (or the ring formed by taking two independent occurrences of $R^{\circ}$ together with their intervening atoms), are independently halogen, $—(CH_2)_{0-2}R^{\bullet}$, -(halo$R^{\bullet}$), $—(CH_2)_{0-2}OH$, $—(CH_2)_{0-2}OR^{\bullet}$, $—(CH_2)_{0-2}CH(OR^{\bullet})_2$; —O(halo$R^{\bullet}$), $—CN$, $—N_3$, $—(CH_2)_{0-2}C(O)R^{\bullet}$, $—(CH_2)_{0-2}C(O)OH$, $—(CH_2)_{0-2}C(O)OR^{\bullet}$, $—(CH_2)_{0-2}SR^{\bullet}$, $—(CH_2)_{0-2}SH$, $—(CH_2)_{0-2}NH_2$, $—(CH_2)_{0-2}NHR^{\bullet}$, $—(CH_2)_{0-2}NR^{\bullet}_2$, $—NO_2$, $—SiR^{\bullet}_3$, $—OSiR^{\bullet}_3$, $—C(O)SR^{\bullet}$, $—(C_{1-4}$ straight or branched alkylene)C(O)$OR^{\bullet}$, or $—SSR^{\bullet}$ wherein each $R^{\bullet}$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^{\circ}$ include ═O and ═S. Suitable divalent substituents on a saturated carbon atom of an "optionally substituted" group include the following: ═O ("oxo"), ═S, $═NNR^*_2$, $═NNHC(O)R^*$, $═NNHC(O)OR^*$, $═NNHS(O)_2R^*$, $═NR^*$, $═NOR^*$, $—O(C(R^*_2))_{2-3}O—$, or $—S(C(R^*_2))_{2-3}S—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable substituents on the aliphatic group of $R^*$ include halogen, $—R^{\bullet}$, -(halo$R^{\bullet}$), —OH, $—OR^{\bullet}$, —O(halo$R^{\bullet}$), —CN, —C(O)OH, $—C(O)OR^{\bullet}$, $—NH_2$, $—NHR^{\bullet}$, $—NR^{\bullet}_2$, or $—NO_2$, wherein each $R^{\bullet}$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable substituents on a substitutable nitrogen of an "optionally substituted" group include $—R^{\dagger}$, $—NR^{\dagger}_2$, $—C(O)R^{\dagger}$, $—C(O)OR^{\dagger}$, $—C(O)C(O)R^{\dagger}$, $—C(O)CH_2C(O)R^{\dagger}$, $—S(O)_2R^{\dagger}$, $—S(O)_2NR^{\dagger}_2$, $—C(S)NR^{\dagger}_2$, $—C(NH)NR^{\dagger}_2$, or $—N(R^{\dagger})S(O)_2R^{\dagger}$; wherein each $R^{\dagger}$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. Suitable substituents on the aliphatic group of $R^{\dagger}$ are independently halogen, $—R^{\bullet}$, -(halo$R^{\bullet}$), —OH, $—OR^{\bullet}$, —O(halo$R^{\bullet}$), —CN, —C(O)OH, $—C(O)OR^{\bullet}$, $—NH_2$, $—NHR^{\bullet}$, $—NR^{\bullet}_2$, or $—NO_2$, wherein each $R^{\bullet}$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Physiological conditions: as used herein, has its art-understood meaning referencing conditions under which cells or organisms live and/or reproduce. In some embodiments, the term refers to conditions of the external or internal milieu that may occur in nature for an organism or cell system. In some embodiments, physiological conditions are those conditions present within the body of a human or non-human animal, especially those conditions present at and/or within a target site of interest. Physiological conditions typically include one or more of, e.g., a temperature within the range of 20-40° C. (and specifically about 37° C.), atmospheric pressure of 1, pH of 6-8, glucose concentration of 1-20 mM, oxygen concentration at atmospheric levels, and gravity as it is encountered on earth.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Sample: As used herein, the term "sample" typically refers to an aliquot of material obtained or derived from a source of interest. In some embodiments, a source of interest is a biological or environmental source. In some embodiments, a source of interest may be or comprise a cell or an organism, such as a microbe, a plant, or an animal (e.g., a human). In some embodiments, a source of interest is or comprises biological tissue or fluid. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. Such a "processed sample" may comprise, for example, materials extracted from a sample or obtained by subjecting a primary sample to one or more techniques such as chromatography, extraction, precipitation, etc.

Subject: As used herein, the term "Subject" refers to any organism to which a provided system is or may be administered, e.g., for experimental, diagnostic, prophylactic, cosmetic, and/or therapeutic purposes. Typical subjects include animals (e.g., mammals such as mice, rats, rabbits, non-human primates, and/or humans). In some embodiments, a subject is a human. In some embodiments, a subject is suffering from or susceptible to one or more disorders or conditions. In some embodiments, a subject displays one or more symptoms of a disorder or condition. In some embodiments, a subject has been diagnosed with one or more disorders or conditions. In some embodiments, the disorder or condition is or includes cancer, or presence of one or more tumors. In some embodiments, the subject is receiving or has received certain therapy to diagnose and/or to treat a disease, disorder, or condition. In some embodiments, a subject refers to a human seeking cosmetic benefit and/or improvement, such as an improvement of appearance and/or feel of skin.

Substantial structural similarity: As used herein, the term "substantial structural similarity" refers to presence of shared structural features at particular positions. In some embodiments, the term "substantial structural similarity" refers to presence and/or identity of structural elements such as, for example: loops, sheets, helices, H-bond donors, H-bond acceptors, glycosylation patterns, salt bridges, disulfide bonds, and combinations thereof. In some embodiments, the term "substantial structural similarity" refers to three dimensional arrangement and/or orientation of atoms or moieties relative to one another (for example: distance and/or angles between or among them between an agent of interest and a reference agent).

Therapeutic agent: As used herein, the phrase "therapeutic agent" in general refers to any agent that elicits a desired pharmacological effect (which may, in some embodiments, be or comprise a cosmetic effect) when administered to an organism. In some embodiments, an agent is considered to exhibit an effect (i.e., to be a therapeutic agent) if it demonstrates a statistically significant effect across an appropriate population. In some embodiments, the appropriate population may be a population of model organisms. In some embodiments, an appropriate population may be defined by particular criteria, such as a certain age group, gender, genetic background, preexisting clinical conditions, etc., or combinations thereof. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a therapeutic agent is one that achieves a cosmetic effect (i.e., is a cosmetic agent). In some embodiments, a therapeutic agent can be used to achieve improvement of appearance and/or feel of skin, and/or another cosmetic benefit.

Treat: As used herein, the term "treat," "treatment," or "treating" refers to partial or complete alleviation, amelioration, delay of onset of, inhibition, prevention, relief, and/or reduction in incidence and/or severity of one or more symptoms or features of a disease, disorder, and/or condition, or achievement of another desired physiological effect (e.g., a desired cosmetic effect such as improvement of appearance and/or feel of skin, such as visible and/or tactile improvement to skin). In some embodiments, treatment comprises administration of an agent which results in a physiological effect. In some embodiments treatment comprises a cosmetic treatment which upon administration improves physical appearance in manner described herein. In some embodiments, treatment may be administered to a subject who does not exhibit signs or features of a disease, disorder, and/or condition (e.g., may be prophylactic). In some embodiments, treatment may be administered to a subject who exhibits only early or mild signs or features of the disease, disorder, and/or condition, for example for the purpose of decreasing the risk of developing pathology associated with the disease, disorder, and/or condition. In some embodiments, treatment may be administered to a subject who exhibits established, severe, and/or late-stage signs of the disease, disorder, or condition.

DETAILED DESCRIPTION OF CERTAIN EMBODIMENTS

As described herein, the present disclosure provides certain technologies relating to enhancing penetration and/or retention of a payload (e.g., which may be or comprise an active agent) at target site which, for example, may be a site in or on skin, for example on, at, in, or below the stratum corneum, epidermis, dermis or underlying hypodermis. In some embodiments, the present disclosure provides a system capable of transporting and/or enhancing transport of a payload across the skin's surface and into a target site. In some embodiments, the present disclosure provides penetrating agents that penetrate into and/or are retained at a target site. In some embodiments, a penetrating agent may comprise a carrier moiety, and a payload moiety, optionally associated with one another via a linker. In some embodiments, a penetrating moiety is or comprises benzothiazole.

For example, the present disclosure demonstrates that, in reconstructed 3-dimensional human skin tissue (EpiDerm™), about 75% of the applied dose of glycine conjugated to CBT (gly-CBT) penetrated the skin within 6 hours. However, only about ⅓rd of the penetrated amount appeared in the acceptor compartment and ⅔rd remained in the skin. Also, surprisingly, a majority of the amount that penetrated into the skin could not be removed even after washing with Triton-X, methanol or dichloromethane. The latter two are commonly used organic solvents to remove molecules from the skin. These strong solvents extract even lipids from the skin. Their inability to extract gly-CBT (e.g., a CBT-containing entity) from the skin indicates surprising ability of CBT to be retained in the skin. The inability to extract gly-CBT (e.g., a CBT-containing entity) from the skin was also observed in porcine skin. The present disclosure teaches that CBT's ability to penetrate into and be retained in the skin can be used for various dermatological and cosmetic applications. In some embodiments, a carrier moiety for use in accordance with the present disclosure, is or comprises CBT or an analog thereof.

In some embodiments, such a carrier moiety (e.g., CBT or an analog thereof) may be linked to or otherwise associated with a payload moiety so that the payload moiety (and/or an active agent component thereof) penetrates and/or is retained within skin (e.g., to an extent and/or for a time greater than it is under comparable conditions absent the CBT).

In some embodiments, a penetrating agent as described herein may include an encapsulating component, such as, for example, a nanoparticle, liposome, micelle, etc., associated with an active agent. In some embodiments, such an encapsulating component may be considered a "linking moiety" to such an extent that it facilitates association of a carrier moiety with a payload moiety (e.g., with an active agent). Alternatively, in some embodiments, such an encapsulating component may be considered to be part of a payload moiety (e.g., which may be or comprise an encapsulating component and an active agent). In some embodiments, an encapsulating component (e.g., nanoparticle(s)) may be prepared from and/or may be biocompatible materials. In some embodiments, an encapsulating component may facilitate association of a payload moiety and/or an active agent with a carrier moiety as described herein and/or may otherwise improve or contribute to improvement of one or more features (e.g., stability) of a payload moiety, active agent and/or penetrating agent. In some embodiments, an encapsulating component (e.g., nanoparticle(s)) has a surface that can be modified with a carrier moiety (e.g., CBT).

In some embodiments, a penetrating agent is formula (I):

(I)

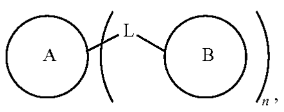

or pharmaceutically acceptable salt thereof, wherein

A is a payload moiety;

B is a carrier moiety;

L is a linker; and n is 1-100.

In some embodiments, n is 1. In some embodiments, n is 2. In some embodiments, n is 3. In some embodiments, n is 5. In some embodiments, n is 10. In some embodiments, n is 20. In some embodiments, n is 50. In some embodiments, n is 1-2. In some embodiments, n is 1-5. In some embodiments, n is 1-50.

In some embodiments, a penetrating agent is formula (I-a):

(I-a)

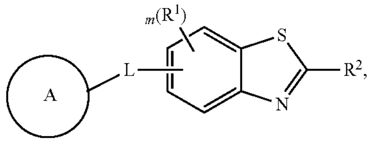

or pharmaceutically acceptable salt thereof, wherein

A is a payload moiety;

L is a linker;

$R^1$ is independently at each occurrence —H, halogen, —CN, optionally substituted $C_{1-6}$ aliphatic, optionally substituted 5-10-membered heterocyclyl, optionally substituted 6- to 10-membered aryl, or optionally substituted 5-10-membered heteroaryl;

$R^2$ is —H, halogen, —CN, optionally substituted $C_{1-6}$ aliphatic, optionally substituted 5-10-membered heterocyclyl, optionally substituted 6- to 10-membered aryl, or optionally substituted 5-10-membered heteroaryl; and m is 1-4.

In some embodiments, a penetrating agent is formula (I-a):

(I-a)

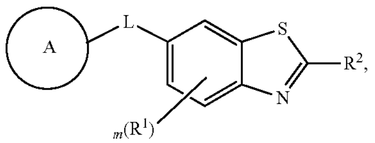

or pharmaceutically acceptable salt thereof, wherein A, L, $R^1$, $R^2$, and m are defined herein.

In some embodiments, a penetrating agent is formula (I-b):

(I-b)

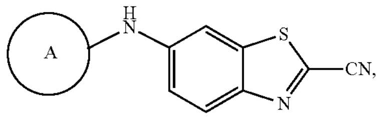

or pharmaceutically acceptable salt thereof, wherein A is defined herein.

In some embodiments, a penetrating agent is formula (I-c):

(I-c)

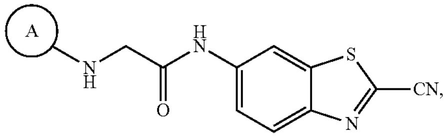

or pharmaceutically acceptable salt thereof,
wherein A is defined herein.

In some embodiments, a penetrating agent is formula (I-d):

(I-d)

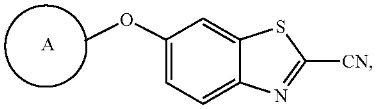

or pharmaceutically acceptable salt thereof,
wherein A is defined herein.

In some embodiments, a penetrating agent is formula (II):

(II)

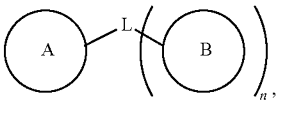

or pharmaceutically acceptable salt thereof,
wherein

A is a payload moiety;
B is a carrier moiety;
L is a linker; and
n is 1-100.

Carrier Moiety

In some embodiments, a system provided and/or utilized in accordance with the present disclosure may comprise one or more carrier and payload moieties, optionally associated with one another via a linker(s).

In some embodiments, the present disclosure provides an insight that certain carrier moieties surprisingly can impart to a penetrating agent as described herein an ability to exhibit penetration into skin to a desired extent (e.g., fraction of administered agent that enters skin and/or depth to which administered agent penetrates—for example degree to which an administered agent penetrates to a target site of interest) and/or retention in (e.g., time for which penetrating agent persists in skin, for example at a target site of interest) skin.

In those embodiments that may comprise a plurality of carrier moieties, such carrier moieties may, in some embodiments all be the same; in other embodiments, a provided system may comprise a plurality of distinct carrier moieties.

For example, in some embodiments, a carrier moiety useful in accordance with the present disclosure is characterized by a particular degree of lipophilicity, for example, when associated (e.g., linked) with a particular payload moiety. In some embodiments, CBT represents a carrier moiety that can be linked with a payload moiety in a useful penetrating agent as described herein. Those skilled in the art, reading the present disclosure, will appreciate that, in some embodiments, lipophilicity of a penetrating agent comprising a particular payload moiety may be adjusted, for example through linkage of a plurality of hydrophobic moieties (e.g., hydrophobic carrier moieties), which may be the same or different and which, individually or together, may be considered or constitute a carrier moiety as described herein.

In some embodiments, a carrier moiety may be or comprise optionally substituted benzothiazole. In some embodiments, a carrier moiety may be or comprise cyanobenzothiazole (CBT). In some embodiments, a carrier moiety may be or comprise 2-cyano-6-hydroxybenzothiazole. In some embodiments, a carrier moiety may be or comprise D-luciferin, L-luciferin, D-Aminoluciferin, or L-Aminoluciferin. In some embodiments, a carrier moiety may be or comprise a molecule other than benzothiazole.

In some embodiments, a carrier moiety may be or comprise a moiety of formula (III):

(III)

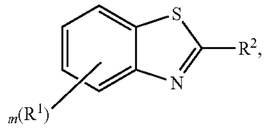

wherein $R^1$, $R^2$, and m are defined herein.

In some embodiments, a carrier moiety may be or comprise a moiety of formula (III-a)

(III-a)

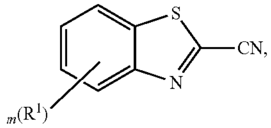

wherein $R^1$ and m are defined herein.

In some embodiments, a carrier moiety may be or comprise a moiety of formula (III-b):

(III-b)

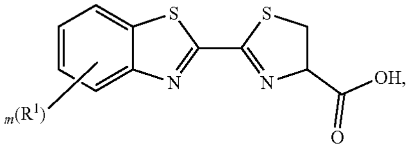

wherein $R^1$ and m are defined herein.

Without wishing to be bound by any particular theory, the present disclosure proposes that carrier moieties as described herein (e.g., CBT and/or analogs thereof, or otherwise appropriately lipophilic entities) may interact with one or more extracellular matrix proteins found in skin (e.g., keratin, elastic, collagen, etc.) or mucosa, with sufficient strength (e.g., as may be characterized, for example, by measurement of Ka and/or Kd, and/or assessment of stability to expected disruption conditions, such as presence of a solvent such as Triton-X, methanol and/or dichloromethane). It will be appreciated by a person of skill in the art, upon reading the present disclosure that carrier moieties may interact with a target area, for example, skin or mucosa, through hydrophobic interactions. In addition, it will also be appreciated that carrier moieties, in some embodiments, may interact with a target area through covalent conjugation or ionic interactions.

In some embodiments, a carrier moiety as described herein can be used to retain and target actives, for example within one or more bodily tissues that may be characterized by high levels of those ECM proteins found in the skin. In some embodiments, ECM proteins found in the skin include, but are not limited, to keratin, elastin, or collagen. It will be appreciated by a person of skill in the art reading the present disclosure that, in some embodiments, a bodily tissue may comprise a mucous membrane.

Additional chemical structures of benzothiazoles include, but are not limited to, those described in European Journal of Medicinal Chemistry, 5 Jun. 2015, Vol. 97, pp. 911-92'7, Curr Top Med Chem. 2017; 17(2):208-237, PLANT SOIL ENVIRON., 51, 2005 (11): 496-505, Medicinal Chemistry Research, September 2012, Volume 21, Issue 9, pp 2644-2651.

Linkers

In some embodiments, a system that can penetrate skin comprises a linker which conjugates a carrier moiety and a payload (which typically will be or comprise an active agent). In some embodiments, a linker moiety is referred to as "L". In some embodiments, a linker may be degradable under biological conditions. In some embodiments, a linker may be non-degradable under biological conditions. In some embodiments, a linker may degrade via hydrolysis or enzymatic reaction. In some embodiments, a linker may be cleavable through application of a cleavage promoter (e.g., an electrical, chemical, and/or enzymatic stimulus). In some embodiments, a linker degrades (e.g., over and/or within a specified period of time, such as within hours, days, weeks, or months) after administration of the system.

In some embodiments, conjugation of a carrier moiety and payload moiety can be mediated by a chemical reaction with an amine group. In some embodiments, a linker may comprise an amine group. In some embodiments, a linker may comprise an amide group. In some embodiments, a linker may be a bond.

In some embodiments, a penetrating agent as described herein may include an encapsulating component; in some such embodiments, association of a carrier moiety with a payload moiety as described herein may be via such encapsulating component. A variety of technologies are available for conjugating or associating a carrier to an encapsulating component, e.g., liposomes, nanoparticles, micelles, etc.

In some embodiments, association between a carrier moiety and payload moiety as described herein may involve chemical conjugation; in some embodiments chemical conjugation may be or comprise click chemistry. In some embodiments, a payload moiety may be or comprise a polypeptide; in some such embodiments, linkage with a polypeptide may be or comprise conjugation with a heteroatom containing residue such as, for example, a threonine, cysteine, or lysine. In some embodiments, linkage with a polypeptide may be via chemical conjugation with a cysteine residue. In some particular embodiments, a carrier moiety such as a CBT may be conjugated (e.g., via click chemistry) to a cysteine moiety of a peptide or a protein.

In some embodiments, L is an optionally substituted $C_{1-6}$ alkylene chain wherein one, two, or three methylene units of L are optionally and independently replaced by —NH—, —O—, —S—, —S(O)—, —$S(O)_2$—, or —C(O)—. A variety of techniques may be used for conjugating or associating the carrier to an active agent.

In some embodiments, L is selected from the group consisting of —NH—, —O—, —S—, —S(O)—, —$S(O)_2$—, and —C(O)—. In some embodiments, L is —NH—. In some embodiments, L is —O—. In some embodiments, L is —S—. In some embodiments, L is —S(O)—. In some embodiments, L is —$S(O)_2$—. In some embodiments, L is —C(O)NH—. In some embodiments, L is —NHC(O)—. In some embodiments, L is —C(O)—.

In some embodiments, L is polyethylene glycol (PEG). In some embodiments, L may be an ethylene diamine, e.g., a polyethylene glycol diamine, etc.

In some embodiments, L comprises a moiety which results from a "click" reaction. In some embodiments, L comprises a triazole. In some embodiments, L comprises an imine. In some embodiments, L comprises an oxime. In some embodiments, L comprises a hydrazine. In some embodiments, L comprises a moiety which results from a nucleophilic addition. In some embodiments, L comprises a moiety which results from a Michael addition. In some embodiments, L comprises a thiol-ene.

In some embodiments, a payload moiety or active agent may be a low molecular weight compound or small molecule; those skilled in the art are aware of a variety of technologies that may be utilized to conjugate a low molecular weight compound or small molecule to a carrier moiety.

As noted herein, those skilled in the art are aware of a variety of technologies for conjugating a carrier moiety to an encapsulating component as described herein.

Payload Moieties

In some embodiments, a system provided and/or utilized in accordance with the present disclosure may comprise one or more carrier and payload moieties, optionally associated with one another via a linker(s).

In some embodiments, a payload moiety may be or comprise a therapeutic agent. In some embodiments a therapeutic agent is or comprises a polypeptide, protein, amino acid, antibody, peptidomimetic, lipid, small molecule, glycosaminoglycan, a nucleic acid, or a combination thereof. In some embodiments, suitable therapeutic agents may be selected from dermatological agents, anti-neoplastic agents, immunological agents, and neurological agents among others. In some embodiments, suitable dermatological active agents may include, for example, local anesthetics, anti-inflammatory, anti-proliferatives, anti-infectives (such as anti-virals, anti-fungals, or anti-bacterial), and active agents to treat a medical condition of the skin.

Examples of suitable glycosaminoglycan include, but are not limited to, heparan sulphate, heparin, chondroitin sulphate, dermatan sulphate, and keratan sulphate. In some embodiments, a glycosaminoglycan may be in the form of a glycosaminoglycan-based protein glycan, including for example, versican, perlecan, glypican, syndecan, decorin. It will be appreciated by a person of skill in the art, upon reading the present disclosure, that certain payload moieties, such as glycosaminoglycan moieties, when incorporated with a carrier moiety (e.g. CBT), will associate with ions and water molecules, to form a hydrated composite. Administration of such an embodiment may bind a mucosal membrane, for example, mucosa of the eye, lip, mouth, vagina, upper respiratory tract (i.e. nose and nasal passages, paranasal sinuses, pharynx, and portion of the larynx above the vocal folds (cords)), lungs, GI tract, urethral opening, and anus. It will be appreciated by a person of skill in the art that such an embodiment would form a barrier to pathogen entry while serving to recruit proteins, for example, cytokines and growth factors.

In those embodiments that may comprise a plurality of payload moieties, such payload moieties may, in some embodiments, all be the same; in other embodiments, a provided system may comprise a plurality of distinct payload moieties.

In some embodiments, a therapeutic agent is described in U.S. Pat. No. 8,791,062, incorporated by reference herein.

In some embodiments, a suitable dermatological agent is selected from: 16-17A-Epoxyprogesterone (CAS Registry Number: 1097-51-4), P-methoxycinnamic acid/4-Methoxycinnamic acid (CAS Registry Number: 830-09-1), Octyl Methoxycinnamate (CAS Registry Number: 5466-77-3), Methyl p-methoxy cinnamate (CAS Registry Number: 832-01-9), 4-ESTREN-17β-OL-3-ONE (CAS Registry Number: 62-90-8), Ethyl-p-anisoyl acetate (CAS Registry Number: 2881-83-6), Dihydrouracil (CAS Registry Number: 1904-98-9), Lopinavir (CAS Registry Number: 192725-17-0), RITANSERIN (CAS Registry Number: 87051-43-2), Nilotinib (CAS Registry Number: 641571-10-0); Rocuronium bromide (CAS Registry Number: 119302-91-9), p-Nitrobenzyl-6-(1-hydroxyethyl)-1-azabicyclo(3.2.0)heptane-3,7-dione-2-carboxylate (CAS Registry Number: 74288-40-7), Abamectin (CAS Registry Number: 71751-41-2), Paliperidone (CAS Registry Number: 144598-75-4), Gemifloxacin (CAS Registry Number: 175463-14-6), Valrubicin (CAS Registry Number: 56124-62-0), Mizoribine (CAS Registry Number: 50924-49-7), Solifenacin succinate (CAS Registry Number: 242478-38-2), Lapatinib (CAS Registry Number: 231277-92-2), Dydrogesterone (CAS Registry Number: 152-62-5), 2,2-Dichloro-N-[(1R,2S)-3-fluoro-1-hydroxy-1-(4-methylsulfonylphenyl) propan-2-yl]acetamide (CAS Registry Number: 73231-34-2), Tilmicosin (CAS Registry Number: 108050-54-0), Efavirenz (CAS Registry Number: 154598-52-4), Pirarubicin (CAS Registry Number: 72496-41-4), Nateglinide (CAS Registry Number: 105816-04-4), Epirubicin (CAS Registry Number: 56420-45-2), Entecavir (CAS Registry Number: 142217-69-4), Etoricoxib (CAS Registry Number: 202409-33-4), Cilnidipine (CAS Registry Number: 132203-70-4), Doxorubicin hydrochloride (CAS Registry Number: 25316-40-9), Escitalopram (CAS Registry Number: 128196-01-0), Sitagliptin phosphate monohydrate (CAS Registry Number: 654671-77-9), Acitretin (CAS Registry Number: 55079-83-9), Rizatriptan benzoate (CAS Registry Number: 145202-66-0), Doripenem (CAS Registry Number: 148016-81-3), Atracurium besylate (CAS Registry Number: 64228-81-5), Nilutamide (CAS Registry Number: 63612-50-0), 3,4-Dihydroxyphenylethanol (CAS Registry Number: 10597-60-1), KETANSERIN TARTRATE (CAS Registry Number: 83846-83-7), Ozagrel (CAS Registry Number: 82571-53-7), Eprosartan mesylate (CAS Registry Number: 144143-96-4), Ranitidine hydrochloride (CAS Registry Number: 66357-35-5), 6,7-Dihydro-6-mercapto-5H-pyrazolo[1,2-a][1,2,4]triazolium chloride (CAS Registry Number: 153851-71-9), Sulfapyridine (CAS Registry Number: 144-83-2), Teicoplanin (CAS Registry Number: 61036-62-2), Tacrolimus (CAS Registry Number: 104987-11-3), LUMIRACOXIB (CAS Registry Number: 220991-20-8), Allyl alcohol (CAS Registry Number: 107-18-6), Protected meropenem (CAS Registry Number: 96036-02-1), Nelarabine (CAS Registry Number: 121032-29-9), Pimecrolimus (CAS Registry Number: 137071-32-0), 4-[6-Methoxy-7-(3-piperidin-1-ylpropoxy) quinazolin-4-yl]-N-(4-propan-2-yloxyphenyl)piperazine-1-carboxamide (CAS Registry Number: 387867-13-2), Ritonavir (CAS Registry Number: 155213-67-5), Adapalene (CAS Registry Number: 106685-40-9), Aprepitant (CAS Registry Number: 170729-80-3), Eplerenone (CAS Registry Number: 107724-20-9), Rasagiline mesylate (CAS Registry Number: 161735-79-1), Miltefosine (CAS Registry Number: 58066-85-6), Raltegravir potassium (CAS Registry Number: 871038-72-1), Dasatinib monohydrate (CAS Registry Number: 863127-77-9), OXOMEMAZINE (CAS Registry Number: 3689-50-7), Pramipexole (CAS Registry Number: 104632-26-0), PARECOXIB SODIUM (CAS Registry Number: 198470-85-8), Tigecycline (CAS Registry Number: 220620-09-7), Toltrazuril (CAS Registry Number: 69004-03-1), Vinflunine (CAS Registry Number: 162652-95-1), Drospirenone (CAS Registry Number: 67392-87-4), Daptomycin (CAS Registry Number: 103060-53-3), Montelukast sodium (CAS Registry Number: 151767-02-1), Brinzolamide (CAS Registry Number: 138890-62-7), Maraviroc (CAS Registry Number: 376348-65-1), Doxercalciferol (CAS Registry Number: 54573-75-0), Oxolinic acid (CAS Registry Number: 14698-29-4), Daunorubicin hydrochloride (CAS Registry Number: 23541-50-6), Nizatidine (CAS Registry Number: 76963-41-2), Idarubicin (CAS Registry Number: 58957-92-9), FLUOXETINE HYDROCHLORIDE (CAS Registry Number: 59333-67-4), Ascomycin (CAS Registry Number: 11011-38-4), beta-Methyl vinyl phosphate (MAP) (CAS Registry Number: 90776-59-3), Amorolfine (CAS Registry Number: 67467-83-8), Fexofenadine HCl (CAS Registry Number: 83799-24-0), Ketoconazole (CAS Registry Number: 65277-42-1), 9,10-difluoro-2,3-dihydro-3-me-7-oxo-7H-pyrido-1 (CAS Registry Number: 82419-35-0), Terbinafine HCl (CAS Registry Number: 78628-80-5), Amorolfine (CAS Registry Number: 78613-35-1), Methoxsalen (CAS Registry Number: 298-81-7), Olopatadine HCl (CAS Registry Number: 113806 May 6), Zinc Pyrithione (CAS Registry Number: 13463-41-7), Olopatadine HCl (CAS Registry Number: 140462-76-6), Cyclosporine (CAS Registry Number: 59865-13-3), and Botulinum toxin and its analogs and vaccine components.

Protein, Polypeptides and Peptides Actives

In some embodiments, proteins useful in the disclosed systems may include, for example, molecules such as cytokines and their receptors, as well as chimeric proteins including cytokines or their receptors, including, for example tumor necrosis factor alpha and beta, their receptors and their derivatives; renin; growth hormones, including human growth hormone, bovine growth hormone, methione-human growth hormone, des-phenylalanine human growth hormone, and porcine growth hormone; growth hormone releasing factor (GRF); parathyroid and pituitary hormones; thyroid stimulating hormone; human pancreas hormone releasing factor; lipoproteins; colchicine; prolactin; corticotrophin; thyrotropic hormone; oxytocin; vasopressin; somatostatin; lypressin; pancreozymin; leuprolide; alpha-1-antitrypsin; insulin A-chain; insulin B-chain; proinsulin; follicle stimulating hormone; calcitonin; luteinizing hormone; luteinizing hormone releasing hormone (LHRH); LHRH agonists and antagonists; glucagon; clotting factors such as factor VIIIC, factor IX, tissue factor, and von Willebrands factor; anti-clotting factors such as Protein C; atrial natriuretic factor; lung surfactant; a plasminogen activator other than a tissue-type plasminogen activator (t-PA), for example a urokinase; bombesin; thrombin; hemopoietic growth factor; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; chorionic gonadotropin; gonadotropin releasing hormone; bovine somatotropin; porcine somatotropin; a microbial protein, such as beta-lactamase;

DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, 4, -5, or -6 (NT-3, NT-4, NT-5, or NT-6), or a nerve growth factor such as NGF-β; platelet-derived growth factor (PDGF); fibroblast growth factor such as acidic FGF and basic FGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha (e.g., interferonα2A), -beta, -gamma, -lambda and consensus interferon; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV-1 envelope glycoprotein, gp120, gp160 or fragments thereof; transport proteins; homing receptors; addressins; fertility inhibitors such as the prostaglandins; fertility promoters; regulatory proteins; antibodies (including fragments thereof) and chimeric proteins, such as immunoadhesins; precursors, derivatives, prodrugs and analogues of these compounds, and pharmaceutically acceptable salts of these compounds, or their precursors, derivatives, prodrugs and analogues. In some embodiments, proteins or peptides may be native or recombinant and include, e.g., fusion proteins.

In some embodiments, a payload is or comprises growth hormone. In some embodiments, growth hormone is human growth hormone (hGH), recombinant human growth hormone (rhGH), bovine growth hormone, methione-human growth hormone, des-phenylalanine human growth hormone, and porcine growth hormone; insulin, insulin A-chain, insulin B-chain, and proinsulin; or a growth factor, such as vascular endothelial growth factor (VEGF), nerve growth factor (NGF), platelet-derived growth factor (PDGF), fibroblast growth factor (FGF), epidermal growth factor (EGF), transforming growth factor (TGF), or insulin-like growth factor-I and -II (IGF-I and IGF-II).

In some embodiments, peptides for use in an injectable, biodegradable delivery depots disclosed herein include, but are not limited to, Glucagon-like peptide-1 (GLP-1) and precursors, derivatives, prodrugs and analogues thereof.

Nucleic Acids

In some embodiments, a payload moiety (and/or an active agent) is or comprises a nucleic acid agent. In some embodiments, a nucleic acid agent useful in accordance with the present disclosure may be or comprise a nucleic acid; in some embodiments, a nucleic acid agent useful in accordance with the present disclosure may be or comprise a nucleic acid precursor, derivative, prodrug, analog, etc. In some embodiments, a nucleic acid agent useful in accordance with the present disclosure may be selected from the group consisting of therapeutic nucleotides, nucleosides and analogues thereof; therapeutic oligonucleotides; and therapeutic polynucleotides.

Those of ordinary skill in the art will be aware of a variety of therapeutic nucleic acid agents, many of which may be particularly useful, for example, as anticancer agents, antimicrobial agents, and/or antiviral agents.

In some embodiments, suitable nucleic acid agents may include, for example ribozymes, antisense oligodeoxynucleotides, aptamers and siRNA. In some embodiments, suitable nucleoside analogues include, but are not limited to, cytarabine (araCTP), gemcitabine (dFdCTP), and floxuridine (FdUTP). In some embodiments, a suitable nucleic acid active agent is an interfering RNA, e.g., shRNA, miRNA or siRNA. In some embodiments, suitable siRNAs include, for example, IL-7 (Interleukin-7) siRNA, IL-10 (Interleukin-10) siRNA, IL-22 (Interleukin-22) siRNA, IL-23 (Interleukin 23) siRNA, CD86 siRNA, KRT6a (keratin 6A) siRNA, K6a N171K (keratin 6a N171K) siRNA, TNFα (tumor necrosis factor α) siRNA, TNFR1 (tumor necrosis factor receptor-1) siRNA, TACE (tumor necrosis factor (TNF)-α converting enzyme) siRNA, RRM2 (ribonucleotide reductase subunit-2) siRNA, and VEGF (vascular endothelial growth factor) siRNA. mRNA sequences of the human gene targets of these siRNAs are known in the art. For IL-7, see, e.g., GenBank Accession: NM-000880.3, GenBank Accession: NM-001199886.1, GenBank Accession: NM-001199887.1, and GenBank Accession: NM-001199888.1; for IL-10, see, e.g., GenBank Accession: NM-000572.2; for IL-22 see, e.g., GenBank Accession: NM-020525.4; for IL-23, see, e.g., GenBank Accession: NM-016584.2, and GenBank Accession: AF301620.1; for CD86, see, e.g., GenBank Accession: NM-175862.4, GenBank Accession: NM-006889.4, GenBank Accession: NM-176892.1, GenBank Accession: NM-001206924.1, and GenBank Accession: NM-001206925.1; for KRT6a, see, e.g., GenBank Accession: NM-005554.3; for TNFα, see, e.g., GenBank Accession: NM-000594.2; for TNFR1, see, e.g., GenBank Accession: NM-001065.3; for TACE, see, e.g., GenBank Accession: NM-003183.4; for RRM2, see, e.g., GenBank Accession: NM-001165931.1 and GenBank Accession: NM-001034.3; for VEGF, see, e.g., GenBank Accession: NM-001025366.2, GenBank Accession: NM-001025367.2, GenBank Accession: NM-001025368.2, GenBank Accession: NM-001025369.2, GenBank Accession: NM-001025370.2, NM-001033756.2, GenBank Accession: NM-001171622.1, and GenBank Accession: NM-003376.5.

Certain Exemplary Therapeutic and/or Otherwise Active Agents

In some embodiments, the present disclosure provides for, among other things, a penetrating agent comprising a therapeutic agent. In some embodiments, a therapeutic agent or an active agent may be directed to one or more of the following drug targets: Kringle domain, Carboxypeptidase, Carboxylic ester hydrolases, Glycosylases, Rhodopsin-like dopamine receptors, Rhodopsin-like adrenoceptors, Rhodopsin-like histamine receptors, Rhodopsin-like serotonin receptors, Rhodopsin-like short peptide receptors, Rhodopsin-like acetylcholine receptors, Rhodopsin-like nucleotide-like receptors, Rhodopsin-like lipid-like ligand receptors, Rhodopsin-like melatonin receptors, Metalloprotease, Transporter ATPase, Carboxylic ester hydrolases, Peroxidase, Lipoxygenase, DOPA decarboxylase, A/G cyclase, Methyltransferases, Sulphonylurea receptors, other transporters (e.g., Dopamine transporter, GABA transporter 1, Norepinephrine transporter, Potassium-transporting ATPase α-chain 1, Sodium-(potassium)-chloride cotransporter 2, Serotonin transporter, Synaptic vesicular amine transporter, and Thiazide-sensitive sodium-chloride cotransporter), Electrochemical nucleoside transporter, Voltage-gated ion channels, GABA receptors (Cys-Loop), Acetylcholine receptors (Cys-Loop), NMDA receptors, 5-HT3 receptors (Cys-Loop), Ligand-gated ion channels Glu: kainite, AMPA Glu receptors, Acid-sensing ion channels aldosterone, Ryanodine receptors, Vitamin K epoxide reductase, MetGluR-like GABAB receptors, Inwardly rectifying K+ channel, NPC1L1, MetGluR-like calcium-sensing receptors, Aldehyde dehydrogenases, Tyrosine 3-hydroxylase, Aldose reductase, Xanthine dehydrogenase, Ribonucleoside reductase, Dihydrofolate reductase, IMP dehydrogenase, Thioredoxin reductase, Dioxygenase, Inositol monophosphatase, Phosphodiesterases, Adenosine deaminase, Peptidylprolyl isomerases, Thymidylate synthase, Aminotransferases, Farnesyl diphosphate synthase, Protein kinases, Carbonic anhydrase, Tubulins, Troponin, Inhibitor of IκB kinase-β, Amine oxidases, Cyclooxygenases, Cytochrome P450s, Thyroxine 5-deiodinase, Steroid dehydrogenase, HMG-CoA reductase, Steroid reductases, Dihydroorotate oxidase, Epoxide hydrolase, Transporter ATPase, Translocator, Glycosyltransferases, Nuclear receptors NR3 receptors, Nuclear receptors: NR1 receptors, or Topoisomerase.

In some embodiments, a therapeutic agent or an active agent targets one of rhodopsin-like GPCRs, nuclear receptors, ligand-gated ion channels, voltage-gated ion channels, penicillin-binding protein, myeloperoxidase-like, sodium: neurotransmitter symporter family, type II DNA topoisomerase, fibronectin type III, or cytochrome P450.

In some embodiments, a therapeutic agent is or comprises an anticancer agent. Suitable anticancer agents include, but are not limited to, Actinomycin D, Alemtuzumab, Allopurinol sodium, Amifostine, Amsacrine, Anastrozole, Ara-CMP, Asparaginase, Azacytadine, Bendamustine, Bevacizumab, Bicalutimide, Bleomycin (e.g., Bleomycin A2 and B2), Bortezomib, Busulfan, Camptothecin sodium salt, Capecitabine, Carboplatin, Carmustine, Cetuximab, Chlorambucil, Cisplatin, Cladribine, Clofarabine, Cyclophosphamide, Cytarabine, Dacarbazine, Dactinomycin, Daunorubicin, Daunorubicin liposomal, Decitabine, Docetaxel, Doxorubicin, Doxorubicin liposomal, Epirubicin, Estramustine, Etoposide, Etoposide phosphate, Exemestane, Floxuridine, Fludarabine, Fludarabine phosphate, 5-Fluorouracil, Fotemustine, Fulvestrant, Gemcitabine, Goserelin, Hexamethylmelamine, Hydroxyurea, Idarubicin, Ifosfamide, Imatinib, Irinotecan, Ixabepilone, Lapatinib, Letrozole, Leuprolide acetate, Lomustine, Mechlorethamine, Melphalan, 6-Mercaptopurine, Methotrexate, Mithramycin, Mitomycin C, Mitotane, Mitoxantrone, Nimustine, Ofatumumab, Oxaliplatin, Paclitaxel, Panitumumab, Pegaspargase, Pemetrexed, Pentostatin, Pertuzumab, Picoplatin, Pipobroman, Plerixafor, Procarbazine, Raltitrexed, Rituximab, Streptozocin, Temozolomide, Teniposide, 6-Thioguanine, Thiotepa, Topotecan, Trastuzumab, Treosulfan, Triethylenemelamine, Trimetrexate, Uracil Nitrogen Mustard, Valrubicin, Vinblastine, Vincristine, Vindesine, Vinorelbine, and analogues, precursors, derivatives and pro-drugs thereof. It should be noted that two or more of the above compounds may be used in combination in a penetrating agent, or a composition comprising a penetrating agent, as described herein.

In some embodiments, a therapeutic agent may be or comprise an opioid or derivative thereof, and/or an opioid receptor agonist or antagonist, e.g., any of naltrexone, naloxone, nalbuphine, fentanyl, sufentanil, oxycodone, or a pharmaceutically acceptable salt or derivatives thereof.

In some embodiments, a therapeutic agent or an active agent is a small molecule or low molecular weight compound, e.g., a molecule or compound having a molecular weight of less than or equal to about 1000 Daltons, e.g., less than or equal to about 800 Daltons.

In some embodiments, a therapeutic agent or an active agent is or comprises a label. Suitable labels include, e.g, radioactive isotopes, fluorescers, chemiluminescers, chromophores, enzymes, enzyme substrates, enzyme cofactors, enzyme inhibitors, dyes, metal ions, magnetic particles, nanoparticles and quantum dots.

In some embodiments, a therapeutic agent or an active agent may be present in any suitable concentration in the compositions disclosed herein. Suitable concentrations may vary depending on the potency of the relevant agent, its half-life, etc. In addition, in some embodiments, penetrating agent compositions according to the present disclosure may include one or more active agents, e.g., a combination of two or more of the active agents described above.

Nanoparticles

In some embodiments, an agent is or comprises a nanoparticle. In some embodiments, an agent is encapsulated within a nanoparticle. In some embodiments, examples of materials used to make nanoparticles include organic polymers such as polylactic co-glycolic acid, polyanhydride, hyaluronic acid, as well as inorganic materials such as gold, silica, and iron oxide, among others. In some embodiments, nanoparticles can also be made of lipids forming liposomes or solid lipid nanoparticles. In some embodiments, nanoparticles can encapsulate cosmetic actives including but not limited to vitamins, anti-oxidants, colorants, fragrances, and sun screens. In one embodiment, the size, shape, or elasticity of the nanoparticles is chosen so as to preferentially induce their localization in the superficial skin layers.

In some embodiments, a carrier moiety (e.g., CBT) is conjugated to nanoparticles using a linker. In some embodiments, a linker that conjugates a carrier moiety to a nanoparticle may be selected from glycine, other amino acids, polyethylene glycol, succinic acid, adipic acid dihydrazide, among others.

Cosmetic Actives

In some embodiments, a provided penetrating agent includes a payload or active agent that is a cosmetic agent. Those skilled in the art are aware of a variety of cosmetic agents including, for example, those described in in US 2006/0008428A1, which is incorporated herein. In some embodiments, a cosmetic agent may be or comprise a compound or mixture of compounds, in purified form or in complex form, especially mineral or plant-based, exhibiting an intrinsic activity in vitro or in vivo, and capable of formulation within a cosmetic product.

As those skilled in the art are aware, a composition considered to be a "cosmetic product" is any substance or preparation intended to be brought into contact with the various surface parts of the human body (epidermis, body-hair and head-hair system, nails, lips and external genital organs) or with the teeth and the buccal mucosae for the purpose, exclusively or principally, of cleaning them, of fragrancing them, of modifying their appearance and/or of correcting body odors and/or of protecting them or of keeping them in good condition (Cosmetics Directive 76/768/EEC, amended).

In some embodiments, a payload moiety or active included in a penetrating agent as described herein is or comprises one or more cosmetic actives. Alternatively or additionally, in some embodiments, a formulation of a penetrating agent as described herein may include one or more such cosmetic actives. In some embodiments, cosmetic actives may include, but not be limited, safe and effective amount of skin care agents selected from the groups consisting of glycosaminoglycans, amino acids, peptides and derivatives thereof, desquamatory actives, vitamins and derivatives thereof, retinoids and derivatives thereof, hydroxy acids, anti-acne actives, radical scavengers, chelators, anti-inflammatory agents, topical anesthetics, moisturizers, emollients, skin conditioners, antiperspirants, anti-oxidants, anti-wrinkle products, surfactants, deodorants, colorants, pigments, sunscreens or other photo protectants, tanning actives, skin lightening agents, anti-cellulite agents, probiotics/prebiotics, flavonoids, antimicrobial actives, skin healing agents, perfumes or fragrances, cannabinoids. In some embodiments, a provided system comprises a compound identified within OTC monographs. In some embodiments, a compound identified within OTC monographs includes, for example, other Anti-acne products, Topical anti-fungal, Anti-microbial products, Antiperspirant, Astringents, Corn & Callus removers, Dandruff products, Hair growth/hair loss, Nailbiting products, Psoriasis, Eczema, Rosacea, skin bleaching, Skin lightening products, Sunscreens, Topical analgesic, Wart removers, insecticides, pharmaceuticals, plus other agents such as farnesol, phytantriol, allantoin, glucosamine, and any other inert or active material intended or otherwise suitable for topical application to the skin mixtures thereof in a dermatologically acceptable carrier.

In some particular embodiments of a penetrating agent as described herein, CBT is conjugated directly (with or without an intermediate linker) to a cosmetic nanoparticle selected from pigment or sunscreen.

Administration of Provided Systems

Technologies as described herein are useful to provide a system at a target site. In some embodiments, a target site is or comprises (e.g., is on or within) a bodily tissue. Described herein are technologies for applying materials to an application site, such that a system is provided at the target site.

For example, in some embodiments, a bodily tissue is or comprises epithelial tissue. In some embodiments, bodily tissue is or comprises connective tissue. In some embodiments, bodily tissue is or comprises nerve tissue. In some embodiments, a bodily tissue is or comprises muscle tissue. In some embodiments, a bodily tissue is or comprises tissue of the eye, tissue of the skin or subcutaneous tissue. In some embodiments, bodily tissue is or comprises subcutaneous fat, corneal epithelium or a mucous membrane.

In many embodiments, a target site is a site that is reached after application to a surface, e.g., a tissue surface. In some embodiments, a tissue surface is a surface of a tissue (e.g., skin, eye, or certain mucous membranes) that is exposed on a surface of an organism. In some embodiments, a tissue surface is a surface of an internal tissue that may, for example, be accessed or exposed by performance of a procedure (e.g., a medical procedure such as a surgical procedure including, for example, an orthoscopic procedure) or process applied to an organism.

In some embodiments, the present disclosure provides systems that can be administered to skin, oral mucosa, vaginal mucosa, eye(s), bladder, nasal mucosa, ear canal, or anal mucosa.

As described herein, the present disclosure provides systems that can be administered to skin. In some embodiments, a provided system is administered topically (e.g., is applied to a skin surface). In some embodiments, a provided system is administered as a transdermal patch.

In some embodiments, a provided system is administered to a subject's face (e.g., full face and/or specific targets of a subject's face such as to lips, lower lip, upper lip, tear troughs, crow's feet, nasolabial folds, forehead, cheeks or combinations thereof). In some embodiments, a provided system is administered to a non-facial site (e.g., knees, neck, décolletage, legs, arms, torso, buttocks or feet). In some embodiments, a provided system is administered to hands (e.g., to the back of a hand). In some embodiments, a provided system is administered to ear lobes.

In some embodiments, site of administration is prepared prior to administration of a provided system. In some embodiments, site of administration is prepared by washing site with tepid water and soap. In some embodiments, site of administration is prepared with a commercial derma roller. In some embodiments, site of administration is prepared through tape stripping. In some embodiments, tape stripping comprises application of Scotch semi-transparent tape to site of administration. In some embodiments, tape stripping further comprises removal of the previously applied of Scotch semi-transparent tape from site of administration. In some embodiments, tape stripping is repeated until site of administration glistens. In some embodiments, tape stripping is repeated at least 40 times.

In some embodiments, site of application is covered after application of a provided system. In some embodiments, site of application is covered with Tegaderm™ type film after application of a provided system.

In some embodiments, skin will be treated with water after administration of a system.

In some embodiments, a system is administered daily. In some embodiments, a system is administered at least once daily. In some embodiments, a system is administered at least twice daily. In some embodiments, a system is administered a 1-5 times daily. In some embodiments, a system is administered a 3-5 times daily. In some embodiments, a system is administered every 3 days. In some embodiments, a system is administered every 7 days. In some embodiments, a system is administered about every 15 days. In some embodiments, a system is administered about every 30 days. In some embodiments, a system is administered about every 60 days. In some embodiments, a system is administered about every 90 days.

In some embodiments, a provided system is administered as or in a sustained-release formulation. In some embodiments, a penetrating agent is provided as or in an emulsion or dispersion.

In some embodiments, a provided system may be present in a particular formulation at a weight (e.g., w/w) percentage within a range between a lower boundary and an upper boundary (inclusive), the upper boundary being larger than the lower boundary, wherein the upper boundary may be about 75%, about 70%, about 65%, about 60%, about 55%, about 50%, about 45%, about 40%, about 35%, about 30%, about 25%, about 20%, about 15%, about 10%, or about 5%, and the lower boundary may be about 70%, about 65%, about 60%, about 55%, about 50%, about 45%, about 40%, about 35%, about 30%, about 25%, about 20%, about 15%, about 10%, about 5% or about 1%. In some embodiments, a formulation comprises about 0.001% w/w to about 5.00% w/w of a system. In some embodiments, a formulation comprises about 0.01% w/w to about 5.00% w/w of a system. In some embodiments, a formulation comprises about 0.1% w/w to about 5.00% w/w of a system. In some embodiments, a formulation comprises about 1% w/w to about 5.00% w/w of a system. In some embodiments, a formulation comprises about 1% w/w to about 3% w/w of a system. In some embodiments, a formulation comprises about 2% w/w of a system. In some embodiments, a formulation comprises PBS and about 2% w/w of a system.

In some embodiments, a formulation comprises a provided system and a cosmetic material. In some embodiments, a formulation comprises about 1% w/w to about 50% w/w of a system. In some embodiments, a formulation comprises about 10% w/w to about 50% w/w of a system. In some embodiments, a formulation comprises about 20% w/w to about 50% w/w of a system. In some embodiments, a formulation comprises about 30% w/w to about 50% w/w of a system. In some embodiments, a formulation comprises about 40% w/w to about 50% w/w of a system. In some embodiments, a formulation comprises about 45% w/w to about 50% w/w of a system.

Various forms of formulations can be used to administer a penetrating agent as described herein, and/or to deliver the relevant payload moiety or active agent to the patient. Pharmaceutically acceptable excipients are also well known to persons of ordinary skill in the art, and are readily available. Those skilled in the art will be aware that choice of excipient will often be determined at least in part by the particular payload moiety or active agent involved, and/or by the particular method used to administer the composition. Accordingly, those skilled in the art will appreciate that a penetrating agent as described herein may be included and/or administered in any of a variety of formulations. In some embodiments, formulations suitable for topical administration may be presented as creams, lotions, liquids, serums, gels, pastes, patches, powders, sprays or foams.

In some embodiments, a provided system may be used to treat a disease, disorder, or condition. In some embodiments, a provided system may be used to treat a disease, disorder, or condition of skin (i.e., a "skin condition"). In some embodiments, a skin condition may be selected from the group consisting of, for example, Acanthosis *nigricans*, Acne, Acne scars, Actinic keratosis, Alopecia areata, Atopic dermatitis, Basal cell carcinoma, Cellulitis, Cold sores Contact dermatitis, Dandruff, Diaper rash, Dry skin, Dermatofibrosarcoma protuberans, Dyshidrotic eczema, Eczema, Genital herpes, Genital warts, Hair loss, Herpes simplex infection, Hidradenitis suppurativa, Hives, Hyperhidrosis, Impetigo, Ichthyosis vulgaris, Keloids and other scars, Keratosis pilaris, Lichen planus, Melanoma, Melasma, Merkel cell carcinoma, Moles, Molluscum contagiosum, onychomycosis, pruritis, Neurodermatitis, skin allergies (such as nickel allergy), Nummular dermatitis, pain Pemphigus, *Pityriasis rosea*, Poison ivy, oak, and sumac, Psoriasis, Psoriatic arthritis, Ringworm, Rosacea, Scabies, Scalp psoriasis, Scleroderma, Sebaceous carcinoma, Seborrheic dermatitis, Seborrheic keratosis, Shingles, Skin cancer, Squamous cell carcinoma, Stasis dermatitis, *Tinea versicolor*, Vitiligo, Warts and Wound healing.

In some embodiments, a provided system may be used to treat a disease, disorder, or condition of a bodily tissue, such as a mucosal membrane. In some embodiments, a provided system may be used to treat a disease, disorder, or condition associated with dryness of eyes, nose, mouth, throat, and vagina. In some embodiments, a condition of a bodily tissue may be selected from anal fissures, anal fistulas, bacterial vaginosis, bad breath, blurred vision, canker sores, cataracts, cervicitis, colitis, colon polyps, color blindness, conjunctivitis, diverticular diseases, dyspareunia, eye pain, glaucoma, gum and tooth problems, hemorrhoids, human papillomavirus (HPV), irritable bowel syndrome, laryngitis, leukoplakia, macular degeneration, nasal and sinus polyps, perianal or anal abscesses, perianal or anal infections, pharyngitis, post-menopausal mucosal dryness, redness of the eye, sinusitis, Sjögren's syndrome, sore throat, thrush, tonsillitis, trichomoniasis, uveitis, and yeast infection.

In some embodiments, a provided system may be used to improve or preserve one or more cosmetic properties of the skin such as pigmentation (including age spots, melasma, vitiligo, lentigos, post inflammatory hyperpigmentation), hair growth, hair color, scarring, dryness, radiance, fine lines and wrinkles, smoothness, elasticity, elastosis, erythema, changes in appearance or structure of nails, unwanted tattoos, thin skin, loss of skin volume due to atrophy (including atrophic scarring), purpura, damage associated with UV light exposure or chemical exposure, dandruff, scaling, sweating, prominent pores, callouses, and other changes associated with chronological aging and photoaging.

EXEMPLIFICATION

The present Examples describe, among other things, certain strategies that may be used to characterize and/or assess penetrating agents (and/or components and/or composition or combinations thereof) as described herein. Such strategies (or their equivalents as will be appreciated by those skilled in the art reading the present disclosure) may be used to assess penetrating agents, components (e.g., moieties), compositions, or combinations thereof for suitability for use in accordance with the present disclosure. In some embodiments, therefore, the present disclosure provides technologies for characterizing and/or selecting useful moieties, linkers, penetrating agents, and/or components, compositions, and/or combinations thereof.

Example 1: Skin Penetration of CBT Modified Molecules

CBT was conjugated to both glycine (gly-CBT) and to hyaluronic acid (HA-CBT) to study the skin penetration of a small active functionalized with CBT and a high molecular weight active functionalized with CBT. HA-CBT was synthesizes utilizing HA with a molecular weight of ~250 kDA and glycine as an intermediate spacer with a degree of substation of approximately 10%, measured with $^1$H NMR.

Frozen, porcine skin was allowed to equilibrate to room temperature, and then cut into ~2×2 cm squares and placed into 0.9 mL of PBS in a 6 well plate. 25 μL of HA-CBT (10 mg/mL in PBS), gly-CBT (1 mg/mL in PBS), and PBS were gently spread on porcine skin to a 1 cm circle with a metal spatula. After spreading the formulations, the 6 well plate was placed into a humidified incubator at 37° C. for 18 h.

A small region in the center of the application area was then excised using a surgical scalpel, and placed into OCT in a biopsy mold. The tissue was snap frozen by placing the biopsy mold directly into a methylpentane, dry ice slurry. The tissue was then sectioned on a cryostat microtome to 20 μm sections. A drop of ProLong Gold was placed on each section and covered with a coverslip prior to imaging. Images were taken on a ZeissAxioPlan2 using a 10× objective and a DAPI filter to visualize the location of CBT.

High fluorescence was observed for both gly-CBT and HA-CBT within the stratum corneum and epidermis and a lower signal in the dermis for both molecules. These results demonstrate that large polymers, such as HA with a molecular weight of 250 kDa, and small hydrophilic molecules, such as glycine, can penetrate the skin after functionalization with CBT.

Example 2: Skin Penetration of Gly-CBT and Tissue Interactions

The penetration and interactions of gly-CBT in human skin was assessed using a 3D human skin model (Mattek EpiDerm™). After allowing the skin tissues to equilibrate with media for 1 h at 37° C. in 6 well plates, the media was replaced with PBS and 100 μL of PBS and gly-CBT (1 mg/mL) were applied on top of 4 skin tissues each. Following 6 h incubation, a single tissue from each group was flash frozen in OCT for cryosectioning and microscopy. For the remaining samples, the liquid which remained on top of the tissue inserts (~100 μL) and the liquid in the acceptor solution (900 μL) was collected. The top of the tissue inserts were then washed 2× with PBS and then the inserts were submerged into 2 mL of a 1:1 PBS:MeOH solution to extract molecules which penetrated the skin. After performing the extraction for 2 h at 37° C., the concentration of gly-CBT was measured in the donor, acceptor, and extract solutions by reading the absorbance at 326 nm with a plate reader. The remaining tissue insert was cryosectioned and imaged using fluorescent microscopy as described in Example 1.

Figure 4:
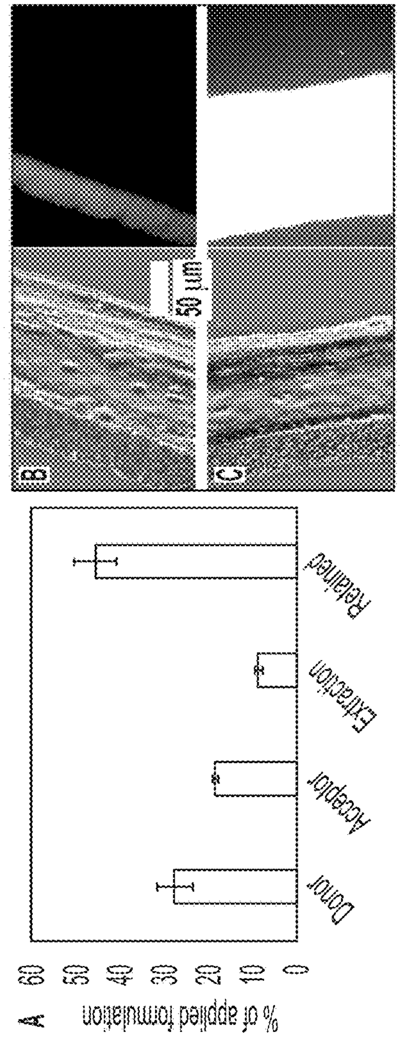
FIG. 4 shows quantification and microscopy of gly-CBT distribution after application on Epiderm-X tissue inserts: fraction of applied gly-CBT which is detected with absorbance in the donor solution, acceptor solution, and extracted from the tissue insert after 6 h incubation (A), bright field (left) and fluorescent image (right) of cryosection of tissue after PBS application (B), and bright field (left) and fluorescent image (right) of cryosection of tissue after gly-CBT application (C).

As shown in FIG. 4, panel A, only ~25% of the gly-CBT which was applied on the surface of the epiderm tissue remained after 6 h incubation, indicating significant penetration. Surprisingly, only ~50% of the total gly-CBT was able to be detected following the extraction procedure and in the donor and acceptor solutions. Only ~10% of the gly-CBT which was applied was able to be extracted from within the Epiderm Tissue; however, a significant fluorescent signal was observed within the tissue with microscopy (FIG. 4, panels C-D).

To further study the penetration of gly-CBT within human skin tissue, HPLC was used to quantify the distribution of different chemical species after application of gly-CBT and gly-aminoLuciferin (gly-Luc) into EpiDerm™ tissue. As described above, 100 μL of gly-CBT and gly-Luc was applied on the top of the skin tissue. Following 6 h incubation, the donor and acceptor solutions were collected and the chemical species which penetrated the skin were attempted to be extracted with 1:1 MeOH:PBS. Following the first extraction protocol, the tissue inserts were rinsed with PBS and imaged in a dark room by exposing with a $UV_{254}$ lamp. Following the imaging, further extractions were carried out sequentially with 1.0% Triton X-100, acidified MeOH (0.1% TFA), and DCM. Neither of the later extractions were successful in extracting out any additional CBT species.

Figure 2:
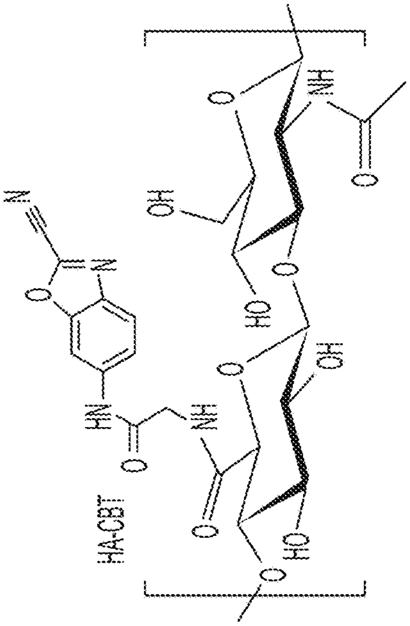
FIG. 2 shows chemical structure of gly-CBT and HA-CBT used for skin penetration studies.
Figure 2:
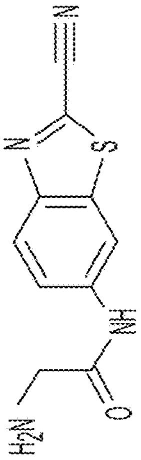
Figure 3:
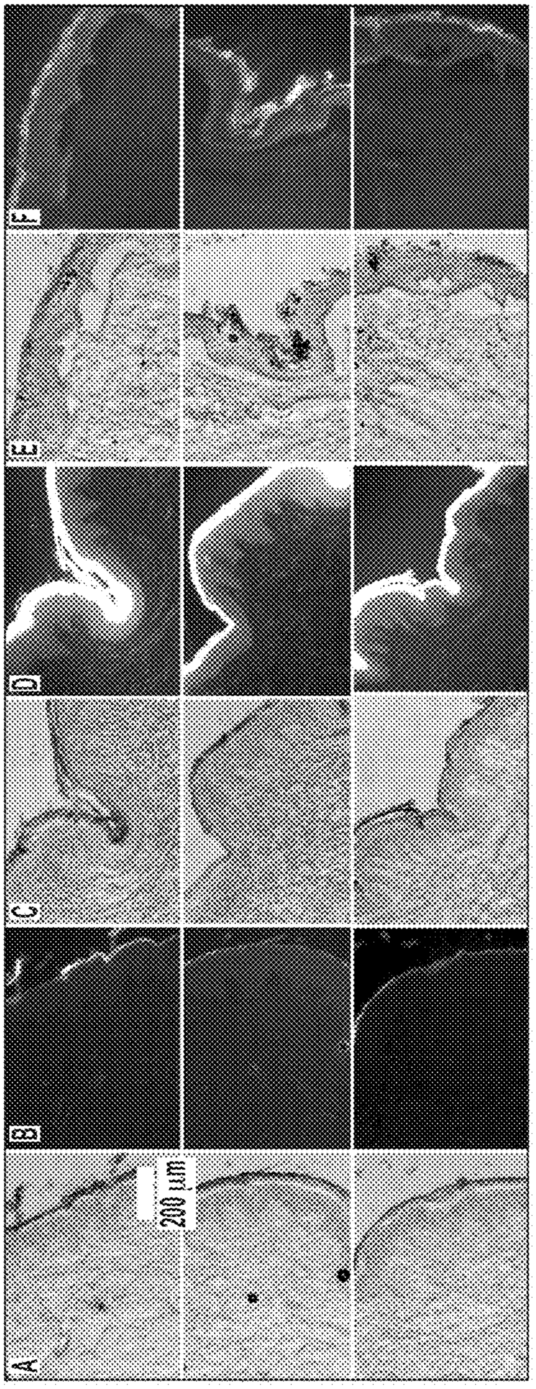
FIG. 3, comprising columns A-F, shows bright field (columns A, C, E) and fluorescent (columns B, D, F) images of porcine skin sections after applications of PBS (columns A, B), gly-CBT (columns C, D), and HA-CBT (columns E, F).
Figure 5:
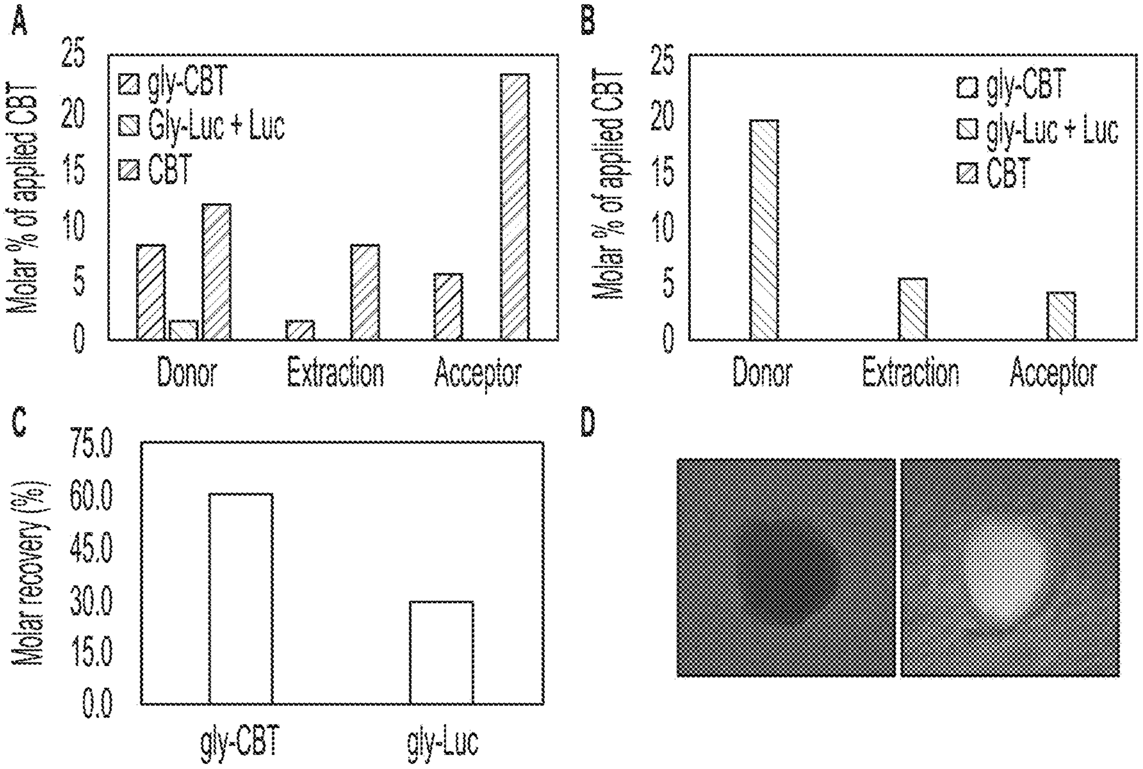
FIG. 5, comprising panels A-D, shows distribution of species of CBT in the donor and acceptor compartments and extracted from the tissue inserts measured with HPLC after application of gly-CBT (A) and gly-Luc (B), fraction of gly-CBT and gly-Luc which was not detected after formulation application (C) and images of tissue inserts (PBS (left) and gly-CBT (right)) under a UV lamp following the extraction of CBT species (D).
Figure 6:
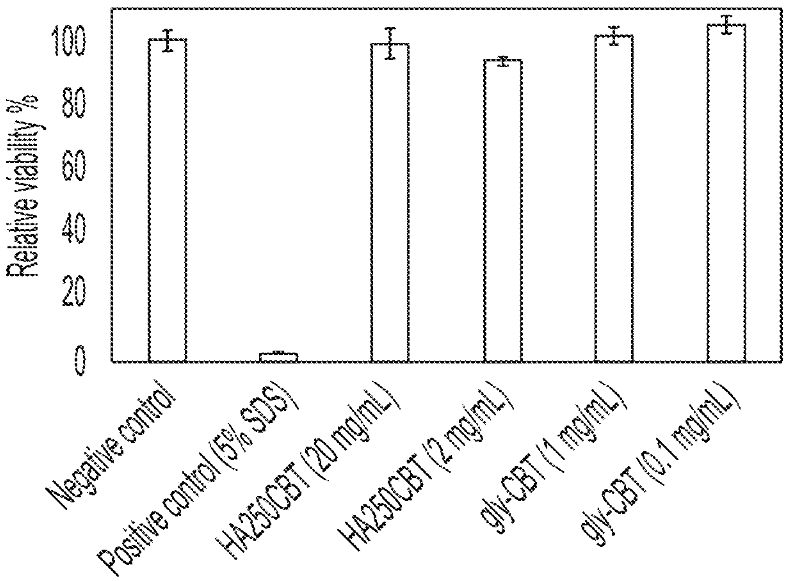
FIG. 6 shows cell viability of epiderm tissue treated with a positive control (5% SDS), HA-CBT, and gly-CBT relative to tissue treated with PBS. Relative cell viability greater than 50% indicates a non-irritant based on the EPI-200-SIT guidelines.

As shown in FIG. 5, panels A-B, <20% of the applied gly-CBT and gly-Luciferin remained in the donor solution after 6h exposure to the tissue. Furthermore, and consistent with the previous study shown in FIG. 2, the total recovery of gly-CBT and gly-Luc was <60% (FIG. 3, panel C). After the first extraction process and washing step, the tissue insert which was exposed to gly-CBT was extremely fluorescent (FIG. 3, panel D). This indicates, that a significant proportion of the gly-CBT which penetrated the Epiderm tissue was unable to be extracted due to interactions with the Epiderm tissue. Surprisingly, neither a surfactant (0.1% Triton X-100 solution), acidified methanol, nor dichloromethane could extract out more CBT species, indicating strong interactions with the skin tissue.

Example 3: Biocompatibility of Topically Applied CBT Functionalized Molecules To evaluate the biocompatibility of CBT functionalized molecules, a skin irritation study was conducted using a 3D reconstructed epidermis model supplied by Mattek. The skin irritation test was conducted following the OECD TG 439 protocol as a basis. Upon receiving the Epiderm™ tissue (Epi-200) from Mattek, the tissue inserts were removed from agarose and incubated in 0.9 mL of media in 6 well plates for 1 h at 37° C. The tissue inserts were then transferred to new wells containing 0.9 mL of fresh media, and incubated overnight for 18 h at 37° C. 30 μL of PBS, HA-CBT (20 mg/mL and 2 mg/mL in PBS), gly-CBT (1 mg/mL and 0.1 mg/mL), and SDS (5 wt %) was applied and spread on the top of 3 independent tissue inserts each. After incubation at 37° C. for 1 h, the formulations were pipetted out and the tissue inserts were washed three times with PBS. The tissue inserts were then incubated in fresh media for 24 h at 37° C. The media was then exchanged with fresh media, and the inserts were incubated for an additional 18 h at 37° C. Following incubation, the viability of the tissue was assessed using the MTT assay, discussed in detail in a protocol established by Mattek (EPI-200-SIT).

While the positive control (5% SDS) showed significant irritation with almost 100% reduction in cell viability in the skin tissue, neither gly-CBT nor HA-CBT showed any reduction in cell viability. This indicates that both CBT modified molecules are non-irritants and are compatible with the human skin tissue.

Example 4: Retention of HA-CBT on Human Skin

To evaluate the retention time of HA-CBT relative to native HA, HA was tagged with an IR label. IR-labeled HA (IR-HA) was synthesized by conjugating CF-647 amine to HA (~50 kDa). CBT was conjugated to IR-HA to yield IR-HA-CBT, with a CBT degree of substitution of 10 mol %.

Frozen human skin was thawed and the stratum corneum (SC) washed gently with soap, then tape stripped 20 times to reduce SC thickness. Tape stripped skin pieces were placed in Franz diffusion cells and equilibrated with PBS over 1 h at 37° C. After equilibration, skin pieces were exposed to either IR-HA (10 mg/mL in PBS) or IR-HA-CBT (10 mg/mL in PBS) for 5 h in the donor compartment in a humidified oven at 37° C. After 5 h, IR-HA and IR-HA-CBT solutions were removed and skin surfaces were washed three times with PBS. Skin was then exposed to PBS overnight in the donor compartment at 37° C. Following incubation in Franz diffusion cells, skin pieces were snap frozen and sectioned on a cryostat. Slides containing cryosections were further washed in PBS at room temperature for 30 min. After this last washing step, slides were mounted with 90% glycerol and imaged on a fluorescent microscope with a Cy5 filter to visualize location of selected IR dye.

Figure 7:
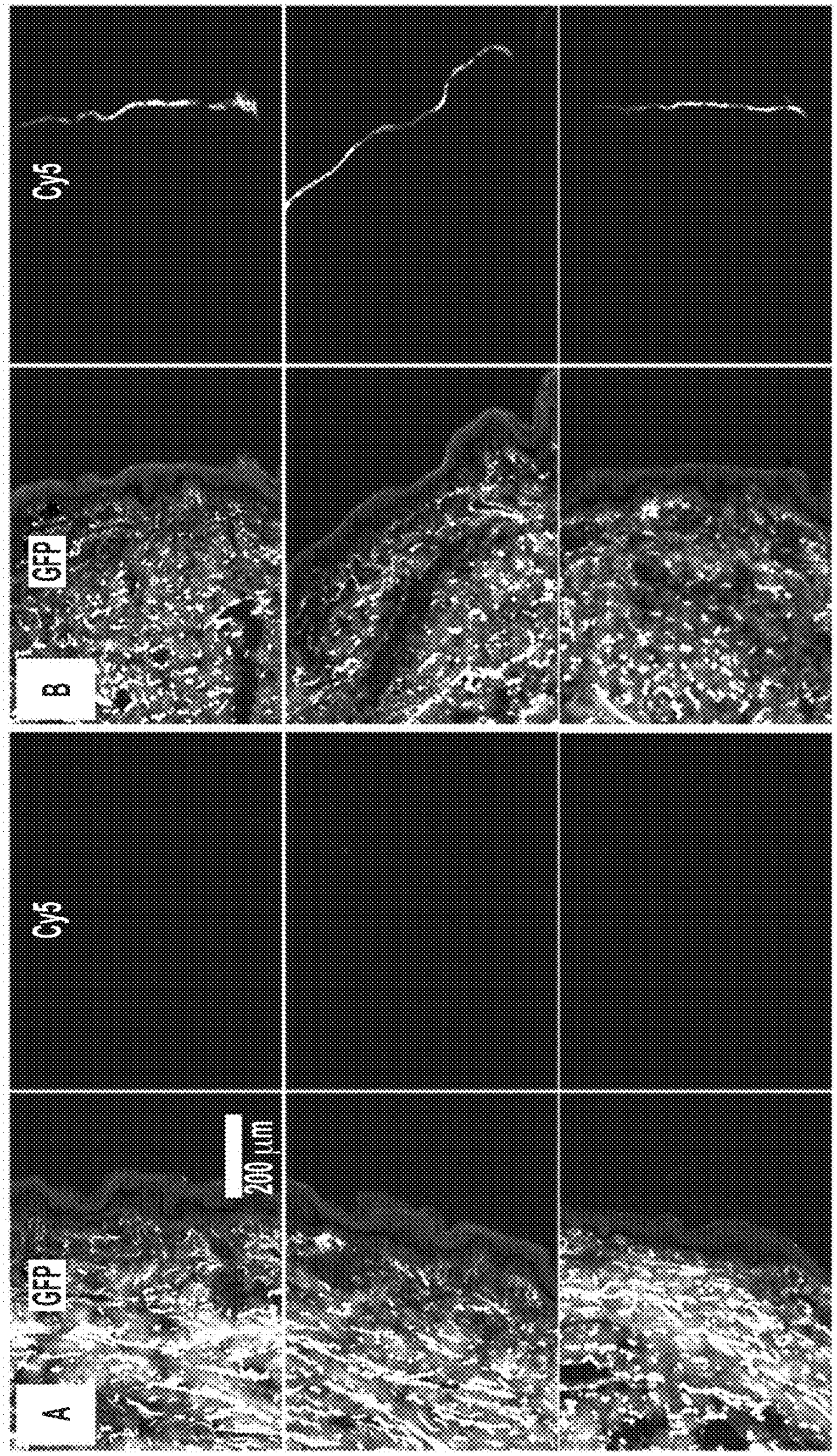
FIG. 7 comprising panels A and B, shows fluorescent images of human skin sections treated with IR-labeled HA (A) and IR-labeled HA-CBT (B). Autofluorescence of skin is observed in both samples (GFP filter), while an IR-labeled HA species is only observed in samples treated with IR-labeled HA-CBT (Cy5 filter).

A strong IR signal was observed in the upper epidermis/SC of skin treated with IR-HA-CBT, while no IR signal was observed in skin treated with IR-HA (FIG. 7). Because skin was tape stripped to reduce thickness of SC, both IR-HA and IR-HA-CBT penetrate skin. However, after vigorous washing steps, which consisted of both washing skin with PBS overnight in Franz cells and washing cryosections on slides in PBS, only IR-HA-CBT was retained by skin samples, demonstrating increased retention of IR-HA in human skin by conjugation to CBT, specifically within upper levels of the epidermis and SC.

We claim:

1. A system comprising a penetrating agent having a structure of formula (I-a):

(I-a)

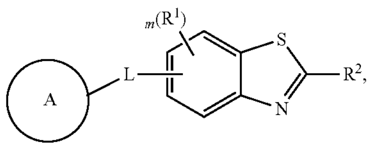

or pharmaceutically acceptable salt thereof, wherein

A is or comprises a glycosaminoglycan;

L is selected from an optionally substituted $C_{1-6}$ alkylene chain wherein one, two, or three methylene units of L are optionally and independently replaced by —NH—, —O—, —S— or —C(O)—, —NH—, —O—, —S—, —S(O)—, —$S(O)_2$—, —C(O)—, polyethylene glycol, and a moiety which results from a click reaction, nucleophilic addition, or Michael addition;

$R^1$ is independently —H, halogen, —CN, optionally substituted $C_{1-6}$ aliphatic, optionally substituted 5- to 10-membered heterocyclyl, optionally substituted 6- to 10-membered aryl, or optionally substituted 5- to 10-membered heteroaryl;

$R^2$ is —H, halogen, —CN, optionally substituted $C_{1-6}$ aliphatic, optionally substituted 5- to 10-membered heterocyclyl, optionally substituted 6- to 10-membered aryl, or optionally substituted 5- to 10-membered heteroaryl; and m is 1-3.

2. The system of claim 1, wherein the penetrating agent has the structure of formula (I-b):

(I-b)

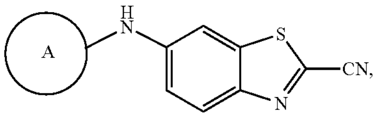

or pharmaceutically acceptable salt thereof.

3. The system of claim 1, wherein the penetrating agent has the structure of formula (I-d):

(I-d)

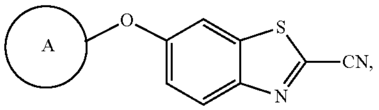

or pharmaceutically acceptable salt thereof.

4. The system of claim 1, wherein m is greater than 1.

5. The system of claim 1, wherein L is degradable under biological conditions.

6. The system of claim 1, wherein the penetrating agent has the structure of formula (I-c):

(I-c)

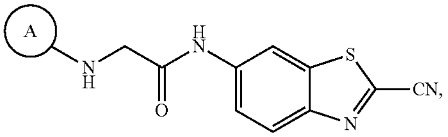

or pharmaceutically acceptable salt thereof.

7. The system of claim 1, wherein the glycosaminoglycan is selected from: hyaluronic acid, heparan sulphate, heparin, chondroitin sulphate, dermatan sulphate, and keratan sulphate.

8. The system of claim 1, wherein the glycosaminoglycan is or comprises hyaluronic acid.

9. The system of claim 1, wherein the glycosaminoglycan is a glycosaminoglycan-based protein glycan.

10. The system of claim 1, wherein the glycosaminoglycan is a glycosaminoglycan-based protein glycan selected from versican, perlecan, glypican, syndecan, and decorin.

11. The system of claim 1, wherein the penetrating agent is characterized by a particular degree of lipophilicity sufficient to enhance penetration and/or retention of the penetrating agent across skin when applied to a surface thereof, relative to that observed for A alone.

* * * * *